United States Patent [19]

Elbe et al.

[11] Patent Number: 4,547,515

[45] Date of Patent: * Oct. 15, 1985

[54] AZOLYL-PHENOXY-TETRAHYDROFU-RAN-2-YLIDENE-METHANE FUNGICIDAL AGENTS

[75] Inventors: Hans-Ludwig Elbe, Wuppertal; Manfred Jautelat; Karl H. Büchel, both of Burscheid; Wilhelm Brandes, Leichlingen; Paul Reinecke; Hans Scheinpflug, both of Leverkusen, all of Fed. Rep. of Germany

[73] Assignee: Bayer Aktiengesellschaft, Leverkusen, Fed. Rep. of Germany

[ * ] Notice: The portion of the term of this patent subsequent to Dec. 11, 2001 has been disclaimed.

[21] Appl. No.: 518,870

[22] Filed: Aug. 1, 1983

[30] Foreign Application Priority Data

Aug. 10, 1982 [DE] Fed. Rep. of Germany ....... 3229734

[51] Int. Cl.⁴ .................... A01N 43/48; A01N 43/50; A01N 43/64
[52] U.S. Cl. .................................... 514/383; 514/397
[58] Field of Search ........................... 424/269, 273 R

[56] References Cited

U.S. PATENT DOCUMENTS 4,259,505 3/1981 Sturm et al. ...................... 548/262

OTHER PUBLICATIONS

Abstract of German Patent 2811916 (9/27/1979).
Abstract of German Patent 2811919 (9/27/1979).

Primary Examiner—Allen J. Robinson
Attorney, Agent, or Firm—Sprung, Horn, Kramer & Woods

[57] ABSTRACT

A composition active against plant fungi comprising a diluent and a plant-fungicidally effective amount of an azolyl-phenoxy-tetrahydrofuran-2-ylidene-methane of the formula

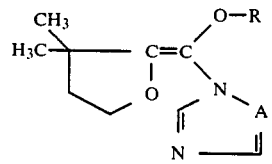

in which
A is a nitrogen atom or the CH group, and
R is optionally substituted phenyl,
or a physiologically acceptable acid addition salt thereof.

10 Claims, No Drawings

AZOLYL-PHENOXY-TETRAHYDROFURAN-2-YLIDENE-METHANE FUNGICIDAL AGENTS

The present invention relates to the use of new azolyl-phenoxy-tetrahydrofuran-2-ylidene-methanes as fungicidal agents.

It has already been disclosed that certain azolylalkenols, such as, for example, 1-(imidazol-1-yl)- and (1,2,4-triazol-1-yl)-2-phenoxy-4,4-dimethyl-1-penten-3-ols which are substituted in the phenoxy part, have good fungicidal properties (compare DE-OS (German Published Specification) No. 2,928,967. However, the action of these compounds is not always completely satisfactory, especially when low amounts and concentrations are used.

It has been found that the new azolyl-phenoxy-tetrahydrofuran-2-ylidene-methanes of the general formula

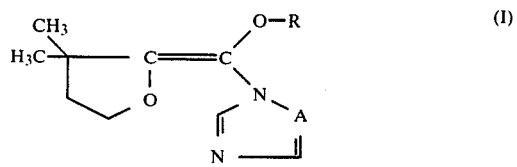

in which
A represents a nitrogen atom or the CH group and
R represents optionally substituted phenyl,
and physiologically acceptable acid addition salts thereof, have good fungicidal properties.

The compounds of the formula (I) can be in two geometric isomer forms, depending on the arrangement of the groups bonded to the double bond; they are preferentially obtained in a varying isomer ratio. The present invention relates both to the individual isomers and to the isomer mixtures.

Surprisingly, the azolyl-phenoxy-tetrahydrofuran-2-ylidene-methanes of the formula (I) to be used according to the invention exhibit a better fungicidal activity than the 1-(imidazol-1-yl)- and (1,2,4-triazol-1-yl)-2-phenoxy-4,4-dimethyl-1-penten-3-ols substituted in the phenoxy part, which are known from the prior art and are closely related compounds chemically and from the point of view of their action. The use of the new substances according to the invention thus represents an enrichment of the art.

The formula (I) provides a general definition of the azolyl-phenoxy-tetrahydrofuran-2-ylidene-methanes to be used according to the invention. Preferably, in this formula,
A represents a nitrogen atom or the CH group and
R represents phenyl which is optionally mono-substituted or di- or tri-substituted by identical or different substituents, preferred substituents which may be mentioned being: halogen, alkyl with 1 to 4 carbon atoms, alkoxy and alkylthio with in each case 1 or 2 carbon atoms, halogenoalkyl, halogenoalkoxy and halogenoalkylthio with in each case 1 or 2 carbon atoms and 1 to 5 identical or different halogen atoms, such as fluorine and chlorine atoms, alkoxycarbonyl with 1 to 4 carbon atoms in the alkyl part, nitro, cyano, and phenyl and phenoxy which are optionally substituted by halogen and/or alkyl with 1 or 2 carbon atoms.

Particularly preferred compounds of the formula (I) are those in which
A represents a nitrogen atom or the CH group and
R represents phenyl which is optionally mono-substituted or di- or tri-substituted by identical or different substituents, preferred substituents which may be mentioned being: fluorine, chlorine, bromine, methyl, ethyl, tert.-butyl, methoxy, ethoxy, methylthio, trifluoromethyl, trifluoromethoxy, trifluoromethylthio, methoxycarbonyl, ethoxycarbonyl, nitro, cyano and phenyl and phenoxy which are optionally substituted by chlorine and/or methyl.

Further preferred compounds according to the invention are addition products of acids and those azolyl-phenoxy-tetrahydrofuran-2-ylidene-methanes of the formula (I) in which the substituents A and R have the meanings which have already been mentioned for these substituents.

Preferred acids which can be added on include hydrogen halides acids, such as, for example, hydrochloric acid and hydrobromic acid, in particular hydrochloric acid, and furthermore phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acid, such as, for example, p-toluenesulphonic acid and 1,5-napthalenedisulphonic acid.

The following compounds of the general formula (I) may be mentioned specifically, in addition to the compounds mentioned in the preparation examples:

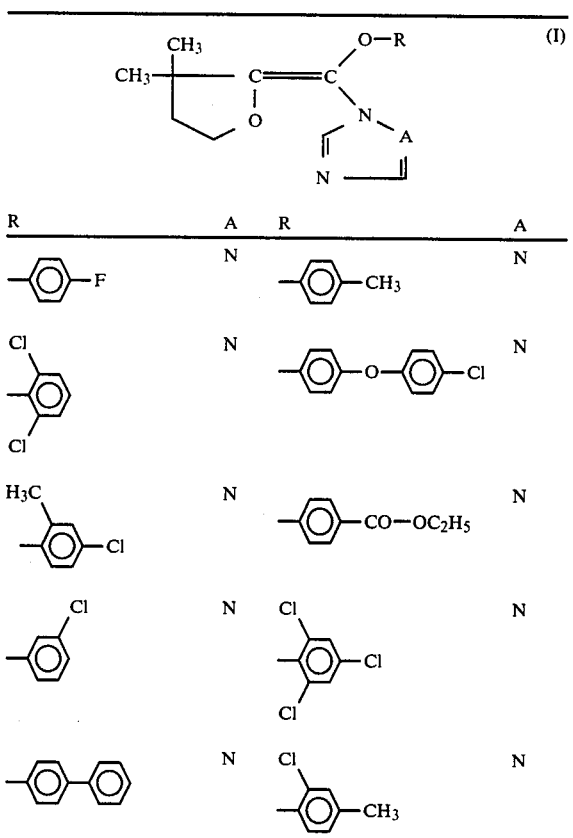

-continued

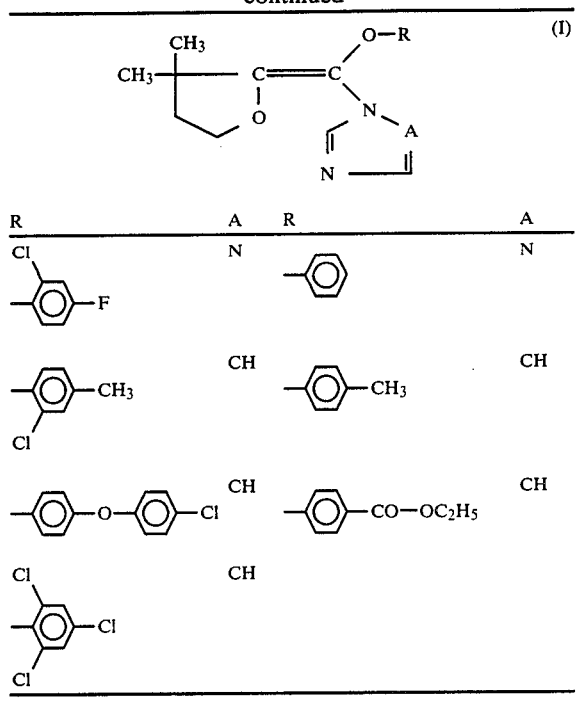

The active compounds to be used according to the invention are the subject of U.S. Pat. No. 4,487,776 and they are obtained by reacting halogenoether-ketones of the formula

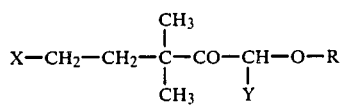

in which
R has the abovementioned meaning and
X and Y represent halogen, preferably chlorine or bromine,
with imidazole or 1,2,4-triazole in the presence of a diluent, such as, for example, toluene, and in the presence of an acid-binding agent, such as, for example, potassium carbonate, at temperatures between 60° and 120° C.

If desired, an acid can then be added on to the compounds of the formula (I) thus obtained.

The halogenoether-ketones of the formula (II) can be prepared by known processes, by reacting halogenoketones of the formula

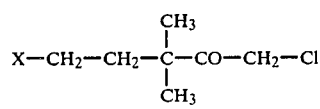

in which
X has the abovementioned meaning,
with known phenols of the formula

 (IV)

in which
R has the abovementioned meaning, in the customary manner, and replacing the remaining active hydrogen in the resulting ether-ketones of the formula

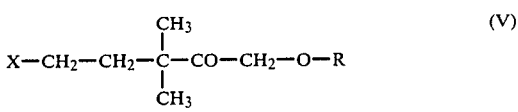

in which
R and X have the abovementioned meaning,
by halogen in the customary manner (compare also the preparation examples). If appropriate, the halogenoether-ketones of the formula (II) can be further reacted directly, without being isolated.

The halogenoketones of the formula (III) are the subject of application Ser. No. 461,369, filed Jan. 27, 1983, now pending, and they are obtained by reacting 2-chloromethylene-3,3-dimethyltetrahydrofuran of the formula

with acidic compounds of the formula

in which
X has the abovementioned meaning,
if appropriate in the presence of an inert organic solvent, such as, for example, toluene or methylene chloride, at temperatures between 20° and 150° C.

2-Chloromethylene-3,3-dimethyltetrahydrofuran of the formula (VI) is the subject of U.S. Pat. No. 4,487,776. It is obtained by successive reaction of 1,1,5-trichloro-3,3-dimethyl-1-pentene (compare German Offenlegungsschrift (German Published Specification) No. 3,029,270) with carboxylates, such as, for example, anhydrous sodium acetate, and with bases, such as, for example, sodium methylate, in the presence of an inert organic solvent, such as, for example, dimethylformamide, at the reflux temperature.

The compounds of the formula (I) to be used according to the invention can also be obtained by a process in which
(a) halogenoketones of the formula (III) are reacted with imidazole or 1,2,4-triazole under the conditions of the abovementioned process (compare the reaction of (II) with azoles), and the azolyltetrahydrofuran-2-ylidene-methanes thus obtained, of the formula

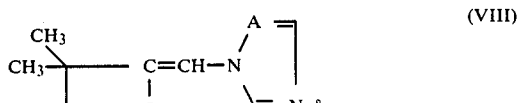

in which
A has the abovementioned meaning,
are then reacted first with a halogen, in particular with bromine, and then with phenols of the formula (IV), in each case in the customary manner; or
(b) 2-chloromethylene-3,3-dimethyltetrahydrofuran of the formula (VI) is reacted with phenols of the formula (IV) in the customary manner, and the phenoxytetrahydrofuran-2-ylidene-methanes thus obtained, of the formula

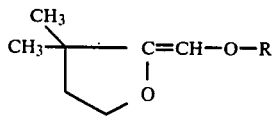  (IX)

in which
R has the abovementioned meaning,
are then reacted first with a halogen, in particular with bromine, in the customary manner and then with imidazole or 1,2,4-triazole under the conditions of the abovementioned process.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtrating, and if appropriate purified by washing with an inert organic solvent.

The active compounds to be used according to the invention exhibit a powerful microbicidal action and can be employed in practice for combating undesired microorganisms. The active compounds are suitable for use as plant protection agents.

Fungicidal agents in plant protection are employed for combating Plasmodiphoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Sphaerotheca species, such as against the powdery mildew of cucumber causative organism (*Sphaerotheca fuliginea*), cereal diseases, such as against the powdery mildew of barley causative organism (*Erysiphe graminis*), and rice diseases, such as *Pyricularia oryzae* and *Pellicularia sasakii.*

When used in appropriate amounts, the active compounds according to the invention also exhibit growth regulating properties.

The active compounds can be converted to the customary formulations, such as solutions, emulsions, wettable powders, suspensions, powders, dusting agents, foams, pastes, soluble powders, granules, aerosols, suspension/emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil, active compound concentrations of 0.00001 to 0.1% by weight, preferably 0.0001 to 0.02%, are required at the place of action.

PREPARATION EXAMPLES

Example 1

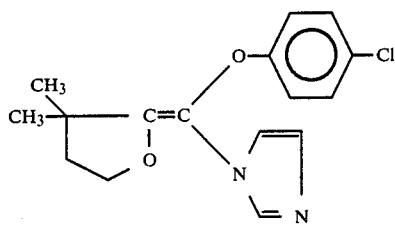

35 g (0.5 mol) of imidazole and 70 g (0.5 mol) of potassium carbonate are dissolved in 700 ml of toluene. 93 g (0.26 mol) of 1-bromo-1-(4-chlorophenoxy)-5-chloro-3,3-dimethyl-2-pentanone in 200 ml of toluene are added to this mixture at 80° C. The reaction mixture is subsequently stirred at 90° C. for 10 hours and is cooled and the inorganic residue is filtered off with suction. The filtrate is washed with water, dried over sodium sulphate and concentrated. The residue is purified by column chromatography (silica gel: ethyl acetate/cyclohexane=3/1). 12.6 g (14.2% of theory) of (4-chlorophenoxy)-(imidazol-1-yl)-(3,3-dimethyltetrahydrofuran-2-ylidene)-methane of melting point 85°-88° C. are obtained.

Preparation of the starting material

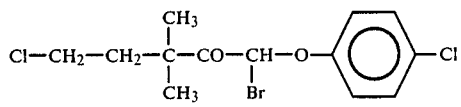

136 g (0.5 mol) of 1-(4-chlorophenoxy)-5-chloro-3,3-dimethyl-2-pentanone are dissolved in 1000 ml of methylene chloride. 79.9 g (1 mol) of bromine are added dropwise at room temperature such that the solution is always decolorized. The reaction mixture is then subsequently stirred at room temperature for 1 hour and is concentrated by distilling off the solvent. A quantitative yield, that is to say 177 g, of 1-bromo-1-(4-chlorophenoxy)-5-chloro-3,3-dimethyl-2-pentanone is obtained, and is further reacted directly.

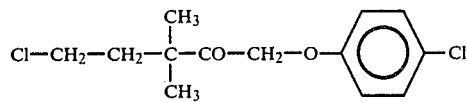

92.5 g (0.72 mol) of 4-chlorophenol and 99.4 g (0.72 mol) of potassium carbonate are heated under reflux in 500 of toluene for 2 hours, during which the water of reaction is distilled off azeotropically. The mixture is cooled to 40° C. and 110 g (0.6 mol) of 1,5-dichloro-3,3-dimethyl-2-pentanone in 300 ml of toluene are added. The reaction mixture is heated to 100° C. for 5 hours and is then cooled, and the inorganic residue is filtered off with suction. The filtrate is washed with dilute sodium hydroxide solution and water, is dried over sodium sulphate and concentrated. 136.3 g (82.6% of theory) of crude 1-(4-chlorophenoxy)-5-chloro-3,3-dimethyl-2-pentanone, which is further reacted directly, are obtained.

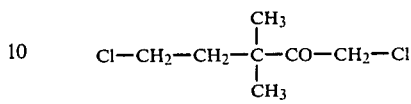

A powerful stream of hydrogen chloride gas is passed from a cylinder into 476 g (3.25 mol) of 2-chloromethylene-3,3-dimethyltetrahydrofuran, while cooling with ice. The gas is absorbed completely, and the internal temperature rises to 30° C. When the reaction mixture is completely saturated with hydrogen chloride, it is subsequently stirred at room temperature for 2 hours. Excess hydrogen chloride is first removed under a water pump, and the mixture is then distilled under a good vacuum. 531 g (90% of theory) of 1,5-dichloro-3,3-dimethyl-2-pentanone of melting point 85°-90° C./0.3 mbar are obtained.

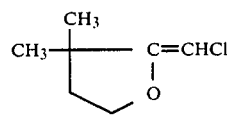

806 g (4 mol) of 1,1,5-trichloro-3,3-dimethyl-1-pentene are heated under reflux with 360 g (4.4 mols) of anhydrous sodium acetate in 1 liter of dimethylformamide for 6 hours. After the mixture has been cooled to about 100° C., 1.6 liters (8 mols) of 30% strength sodium methylate solution in methanol are added dropwise and the mixture is heated under reflux for another 4 hours. The cold solution is poured into water and the mixture is extracted several times with methylene chloride.

After the solution has been dried and the solvent has been distilled off, 654 g of product remain, and are fractionated over a column. 522 g (89% of theory) of 2-chloromethylene-3,3-dimethyltetrahydrofuran of boiling point 84°-87° C./20 mbar are obtained.

The following compounds of the general formula (I)

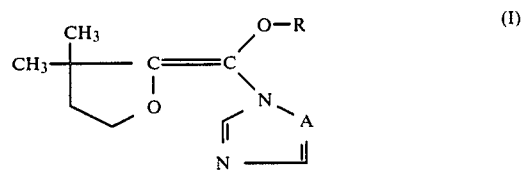

are obtained analogously:

| Example No. | R | A | Melting point (°C.) or $n_D^{20}$ |
|---|---|---|---|
| 2 |  | CH | 214 |

-continued

| Example No. | R | A | Melting point (°C.) or $n_D^{20}$ |
|---|---|---|---|
| 3 | 3,4-diCl-phenyl | CH | 119 (A-Form) |
| 4 | 2,6-diCl-phenyl | CH | 82 |
| 5 | 4-Cl-2-CH₃-phenyl | CH | 109 (A-Form) |
| 6 | 3-Cl-phenyl | CH | 1.5607 |
| 7 | 4-biphenyl | CH | 95–105 |
| 8 | 2,4-diCl-phenyl | CH | 95–105 |
| 9 | 2-Cl-4-F-phenyl | CH | crystal mass |
| 10 | 2-Cl-4-F-phenyl | CH | 118 (A-Form) |
| 11 | 4-Cl-phenyl | N | 124 |
| 12 | 2,4-diCl-phenyl | N | viscous oil |
| 13 | 2,4-diCl-phenyl | N | 115–20 (A-Form) |

-continued

| Example No. | R | A | Melting point (°C.) or $n_D^{20}$ |
|---|---|---|---|
| 14 | 2,4-diCl-phenyl | N | 1.5578 (B-Form) |
| 15 | phenyl | CH | 85–90 |
| 16 | 2,4-diCl-phenyl | N | 104 |

A- and B-form: the two possible isomer forms

Use Examples

The compounds shown below are used as comparison substances in the examples which follow:

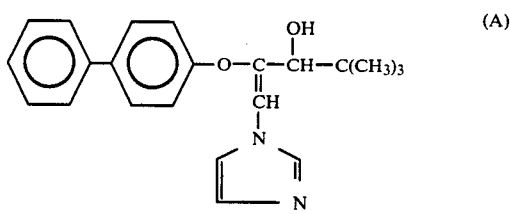

(A)

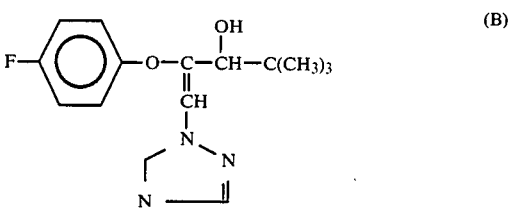

(B)

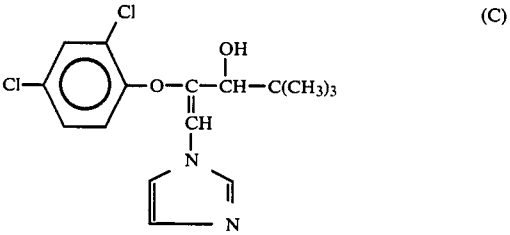

(C)

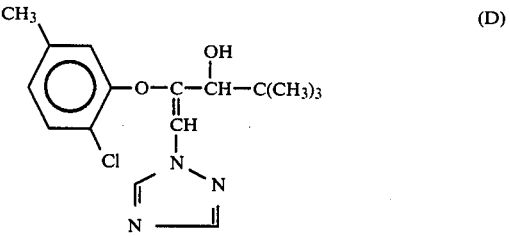

(D)

-continued (E)
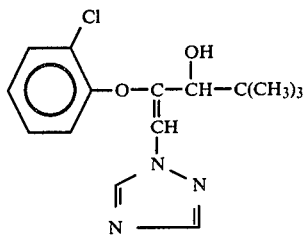

(F)
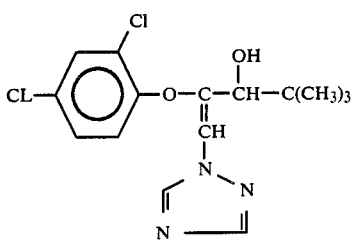

Example A

Sphaerotheca test (cucumber)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus Sphaerotheca fuliginea.

The plants are then placed in a greenhouse at 23° to 24° C. and at a relative atmospheric humidity of about 75%.

Evaluation is carried out 10 days after the inoculation.

In this test, a clearly superior activity compared with the prior art is shown, for example, by the compounds according to the following preparation examples: 11, 1, 2, 3, 8, 4, 5, 6, 12, 9, 10 and 15.

TABLE A

Sphaerotheca test (cucumber)/protective

| Active compound | Infestation in % at an active compound concentration of 0.0005% |
|---|---|
| 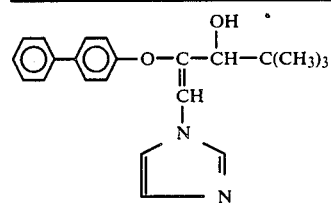 (known) (A) | 62 |

TABLE A-continued

Sphaerotheca test (cucumber)/protective

| Active compound | Infestation in % at an active compound concentration of 0.0005% |
|---|---|
| ![B] (known) (B) | 91 |
| (11) | 12 |
| (1) | 12 |
| (2) | 25 |
| (3) A-Form | 10 |
| (8) | 10 |
| (4) | 10 |

TABLE A-continued

Sphaerotheca test (cucumber)/protective

| Active compound | Infestation in % at an active compound concentration of 0.0005% |
|---|---|
| 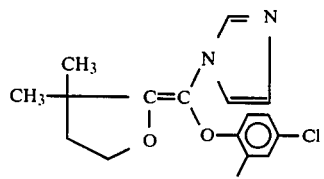 (5) | 10 |
| 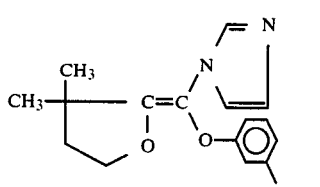 (6) | 50 |
| 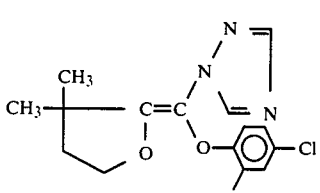 (12) | 0 |
| 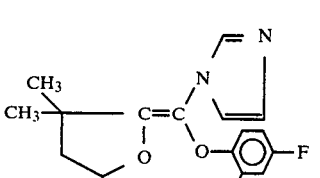 (9) | 0 |
| 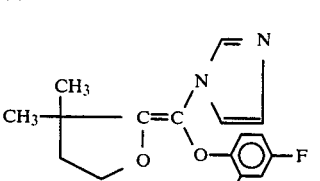 (10) A-Form | 5 |
| 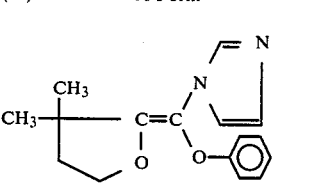 (15) | 20 |

Example B

Erysiphe test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 25° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the following preparation examples: 11, 1, 2, 3, 4, 5, 8 and 6.

TABLE B

Erysiphe test (barley)/protective

| Active compound | Active compound concentration in the spray liquor in % by weight | Disease infestation in % of the untreated control |
|---|---|---|
| 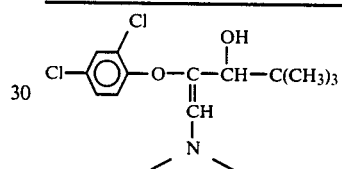 (known) | 0.0025 | 100 |
|  (D) (known) | 0.0025 | 83.8 |
| 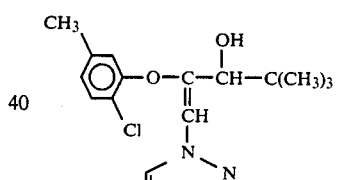 (11) | 0.0025 | 0.0 |
| 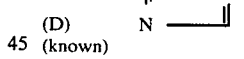 (1) | 0.0025 | 8.8 |
| 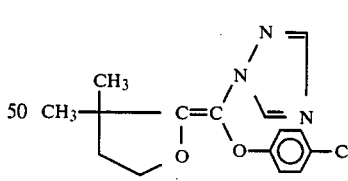 | 0.0025 | 12.5 |

TABLE B-continued

Erysiphe test (barley)/protective

| Active compound | Active compound concentration in the spray liquor in % by weight | Disease infestation in % of the untreated control |
|---|---|---|
| (2) [structure: (CH3)2C(propyl)−C(=N−N=CH−N)−O−(2,4-dichlorophenyl)] | 0.0025 | 8.8 |
| (3) A-Form [structure: similar, O−(2,6-dichlorophenyl)] | 0.0025 | 12.5 |
| (4) [structure: similar, O−(4-Cl-3-CH3-phenyl)] | 0.0025 | 0.0 |
| (5) A-Form [structure: similar, O−(2,4-dichlorophenyl)] | 0.0025 | 8.8 |
| (8) [structure: similar, O−(3-Cl-phenyl)] | 0.0025 | 3.8 |
| (6) | | |

Example C

Pyricularia test (rice)/protective

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples: 2, 3, 4, 6, 7 and 10.

TABLE C

Pyricularia test (rice)/protective

| Active compound | Active compound concentration in % | Disease infestation in % of the untreated control |
|---|---|---|
| (E) (known) [2-Cl-phenoxy with OH, C(CH3)3, triazolyl] | 0.025 | 100 |
| (B) (known) [4-F-phenoxy with OH, C(CH3)3, triazolyl] | 0.025 | 100 |
| (F) (known) [2,4-dichlorophenoxy with OH, C(CH3)3, triazolyl] | 0.025 | 100 |
| (C) (known) [2,4-dichlorophenoxy with OH, C(CH3)3, imidazolyl] | 0.025 | 100 |
| (A) (known) [biphenyloxy with OH, C(CH3)3, imidazolyl] | 0.025 | 100 |

TABLE C-continued

Pyricularia test (rice)/protective

| Active compound | Active compound concentration in % | Disease infestation in % of the untreated control |
|---|---|---|
| 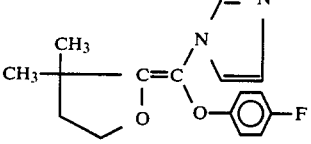 (2) | 0.025 | 13 |
| 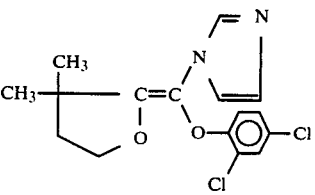 (3) A-Form | 0.025 | 0 |
| 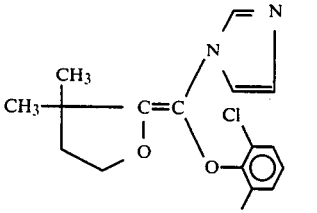 (4) | 0.025 | 25 |
| 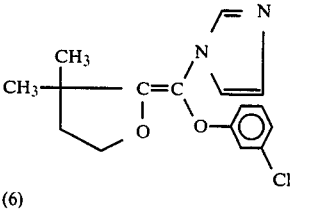 (6) | 0.025 | 0 |
| 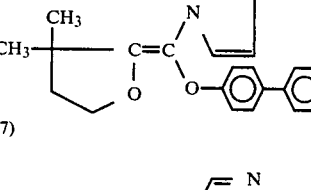 (7) | 0.025 | 25 |
| 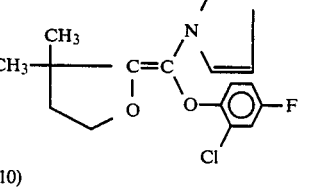 (10) A-form | 0.025 | 0 |

Example D

Pellicularia test (rice)

Solvent: 12.5 parts by weight of acetone

Emulsifier: 0.3 parts by weight of alkylaryl polyglycol ether

To produce a suitable preparation of active compound, 1 part by weight of active compound is mixed with the stated amount of solvent, and the concentrate is diluted with water and the stated amount of emulsifier, to the desired concentration.

To test for activity, young rice plants in the 3 to 4 leaf stage are sprayed until dripping wet. The plants remain in a greenhouse until they have dried off. The plants are then inoculated with Pellicularia sasakii and are placed at 25° C. and 100% relative atmospheric humidity.

The evaluation of the disease infestation is carried out 5 to 8 days after the inoculation.

In this test, a clearly superior activity compared with the prior art is shown, for example, by the compounds according to the following preparation examples: 11, 2, 3, 4, 5, 6, 12 and 10.

TABLE D

Pellicularia test (rice)

| Active compound | Active compound concentration in % | Disease infestation in % of the untreated control |
|---|---|---|
| 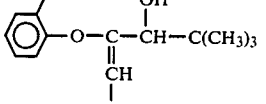 (E) (known) | 0.025 | 100 |
| 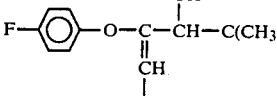 (B) (known) | 0.025 | 50 |
| 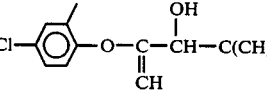 (F) (known) | 0.025 | 100 |
| 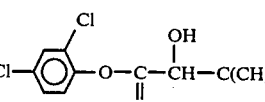 (C) (known) | 0.025 | 100 |

TABLE D-continued

Pellicularia test (rice)

| Active compound | Active compound concentration in % | Disease infestation in % of the untreated control |
|---|---|---|
| (A) (known) | 0.025 | 75 |
| (11) | 0.025 | 13 |
| (2) | 0.025 | 13 |
| (3) A-Form | 0.025 | 0 |
| (4) | 0.025 | 13 |
| (5) | 0.025 | 25 |
| (6) | 0.025 | 13 |
| (12) | 0.025 | 0 |
| (10) A-Form | 0.025 | 0 |

It will be understood that the specification and examples are illustrative but not limitative of the present invention and that other embodiments within the spirit and scope of the invention will suggest themselves to those skilled in the art.

What is claimed is:

1. A process for combating plant pathogenic fungi comprising applying to such fungi, to a plant or to a place where a plant is to be grown, a fungicidally effective amount of an azolyl-phenoxy-tetrahydrofuran-2-ylidene-methane of the formula

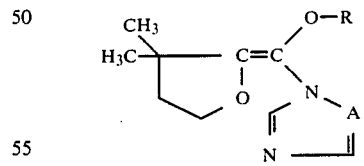

in which
A is a nitrogen atom or the CH group, and
R is phenyl, or phenyl mono-, di- or tri-substituted by substituents independently selected from the group consisting of halogen, alkyl with 1 to 4 carbon atoms, alkoxy or alkylthio each with 1 or 2 carbon atoms, halogenoalkyl, halogenoalkoxy or halogenoalkylthio each with 1 or 2 carbon atoms and 1 to 5 halogen atoms, alkoxycarbonyl with 1 to 4 carbon atoms in the alkyl part, nitro, cyano, phenyl, phenoxy, and phenyl or phenoxy each substituted by at least one of halogen and alkyl with 1 or 2 carbon atoms,
or a physiologically acceptable acid addition salt thereof.

2. A method according to claim 1, in which
R is phenyl, or phenyl mono-, di- or tri-substituted by substituents independently selected from the group consisting of fluorine, chlorine, bromine, methyl, ethyl, tert.-butyl, methoxy, ethoxy, methylthio, trifluoromethyl, trifluoromethoxy, trifluoromethylthio, methoxycarbonyl, ethoxycarbonyl, nitro, cyano, and phenyl or phenoxy each optionally substituted by at least one of chlorine and methyl.

3. A method according to claim 1, wherein such azolyl-phenoxy-tetrahydrofuran-2-ylidene-methane is (4-chlorophenoxy)-(imidazol-1-yl)-(3,3-dimethyltetrahydrofuran-2-ylidene)-methane of the formula

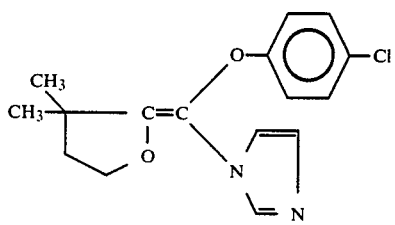

or a physiologically acceptable acid addition salt thereof.

4. A method according to claim 1, wherein such azolyl-phenoxy-tetrahydrofuran-2-ylidene-methane is (4-fluorophenoxy)-(imidazol-1-yl)-3,3-dimethyltetrahydrofuran-2-ylidene)-methane of the formula

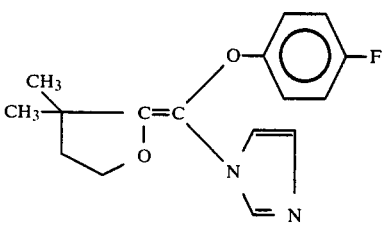

or a physiologically acceptable acid addition salt thereof.

5. A method according to claim 1, wherein such azolyl-phenoxy-tetrahydrofuran-2-ylidene-methane is (2,4-dichlorophenoxy)-(imidazol-1-yl)-(3,3-dimethyltetrahydrofuran-2-ylidene)-methane of the formula

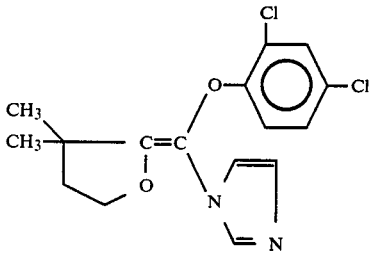

or a physiologically acceptable acid addition salt thereof.

6. A method according to claim 1, wherein such azolyl-phenoxy-tetrahydrofuran-2-ylidene-methane is (4-chloro-2-methylphenoxy)-(imidazol-1-yl)-(3,3-dimethyltetrahydrofuran-2-ylidene)-methane of the formula

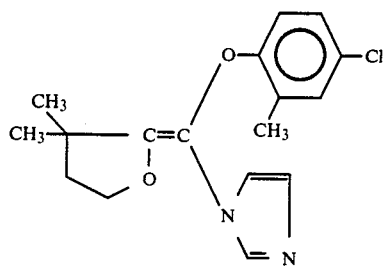

or a physiologically acceptable acid addition salt thereof.

7. A method according to claim 1, wherein such azolyl-phenoxy-tetrahydrofuran-2-ylidene-methane is (3-chlorophenoxy)-(imidazol-1-yl)-(3,3-dimethyltetrahydrofuran-2-ylidene)-methane of the formula

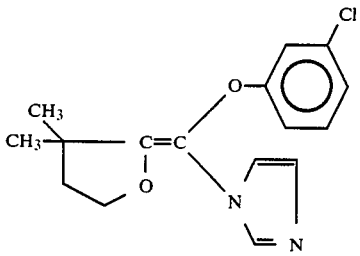

or a physiologically acceptable acid addition salt thereof.

8. A method according to claim 1, wherein such azolyl-phenoxy-tetrahydrofuran-2-ylidene-methane is (2-chloro-4-fluorophenoxy)-(imidazol-1-yl)-(3,3-dimethyltetrahydrofuran-2-ylidene)-methane of the formula

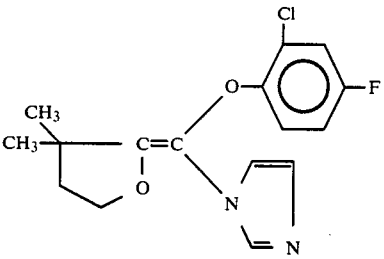

or a physiologically acceptable acid addition salt thereof.

9. A method according to claim 1, wherein such azolyl-phenoxy-tetrahydrofuran-2-ylidene-methane is (4-chlorophenoxy)-(1,2,4-triazol-1-yl)-(3,3-dimethyltetrahydrofuran-2-ylidene)-methane of the formula

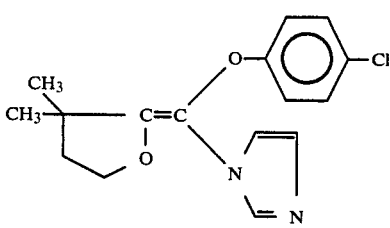

or a physiologically acceptable acid addition salt thereof.
10. A method according to claim 1, wherein such azolyl-phenoxy-tetrahydrofuran-2-ylidene-methane is (2,4-dichlorophenoxy)-(1,2,4-triazol-1-yl)-3,3-dimethyl-tetrahydrofuran-2-ylidene)-methane of the formula
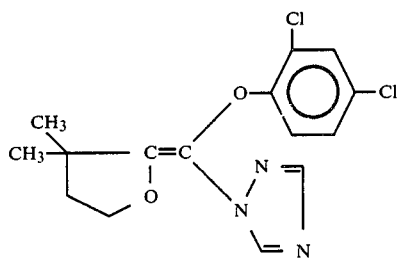
or a physiologically acceptable acid addition salt thereof.
* * * * *

UNITED STATES PATENT AND TRADEMARK OFFICE
CERTIFICATE OF CORRECTION

PATENT NO. : 4,547,515
DATED : October 15, 1985
INVENTOR(S) : Hans-Ludwig Elbe, et al.

It is certified that error appears in the above-identified patent and that said Letters Patent is hereby corrected as shown below:

Col. 22, line 68   Delete bottom right of formula and substitute:

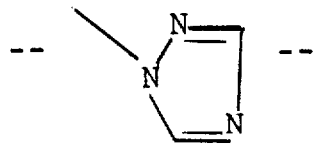

Signed and Sealed this

Twenty-eighth Day of January 1986

[SEAL]

Attest:

DONALD J. QUIGG

Attesting Officer   Commissioner of Patents and Trademarks